United States Patent
Mendelovici et al.

(10) Patent No.: US 7,262,327 B2
(45) Date of Patent: Aug. 28, 2007

(54) RECYCLING PROCESS FOR PREPARING SERTRALINE

(75) Inventors: Marioara Mendelovici, Rechovot (IL); Ben-Zion Dolitzky, Petach Tiqva (IL); Marina Yu Etinger, Nesher (IL); Gennady A. Nisnevich, Haifa (IL)

(73) Assignee: Teva Pharmaceutical Industries Ltd., Petah Tiqva (IL)

(*) Notice: Subject to any disclaimer, the term of this patent is extended or adjusted under 35 U.S.C. 154(b) by 112 days.

(21) Appl. No.: 10/936,190

(22) Filed: Sep. 7, 2004

(65) Prior Publication Data

US 2005/0107636 A1  May 19, 2005

Related U.S. Application Data

(60) Provisional application No. 60/526,451, filed on Dec. 2, 2003, provisional application No. 60/500,875, filed on Sep. 5, 2003.

(51) Int. Cl.
*C07C 209/86* (2006.01)
*C07C 209/88* (2006.01)

(52) U.S. Cl. ............... 564/424; 564/308; 564/425

(58) Field of Classification Search ............... 564/424
See application file for complete search history.

(56) References Cited

U.S. PATENT DOCUMENTS

| 4,536,518 | A | 8/1985 | Welch, Jr. et al. |
| 5,082,970 | A * | 1/1992 | Braish ............... 564/424 |
| 6,452,054 | B2 | 9/2002 | Aronhime et al. |
| 6,495,721 | B1 | 12/2002 | Schwartz et al. |
| 6,500,987 | B1 | 12/2002 | Schwartz et al. |
| 6,600,073 | B1 | 7/2003 | Schwartz et al. |
| 2005/0085669 | A1* | 4/2005 | Hershkovitz et al. ...... 564/428 |
| 2006/0014838 | A1 | 1/2006 | Valluri et al. |

FOREIGN PATENT DOCUMENTS

| WO | WO 97/21662 | 6/1997 |
| WO | WO 98/27050 | 6/1998 |
| WO | WO 99/57093 | 11/1999 |
| WO | WO 01/16089 | 3/2001 |
| WO | 01/49638 A2 * | 7/2001 |
| WO | 01/68566 A1 * | 9/2001 |

* cited by examiner

*Primary Examiner*—Brian Davis
(74) *Attorney, Agent, or Firm*—Kenyon & Kenyon LLP

(57) ABSTRACT

Provided is a recycling process for preparing sertraline, which may be carried out on an industrial scale.

50 Claims, 1 Drawing Sheet

RECYCLING PROCESS FOR PREPARING SERTRALINE

CROSS-REFERENCE TO RELATED APPLICATIONS

This application claims the benefit of U.S. Provisional Application Nos. 60/500,875 filed on Sep. 5, 2003 and 60/526,451 filed on Dec. 2, 2003, the disclosure of which are incorporated by reference in their entirety herein.

FIELD OF THE INVENTION

The present invention relates to recycling processes for preparation of sertraline free of impurities and other stereisomers.

BACKGROUND OF THE INVENTION

Sertraline hydrochloride, (1S-cis)-4-(3,4 dichlorophenyl)-1,2,3,4-tetrahydro-N-methyl-1-naphthalenamine hydrochloride, having the formula:

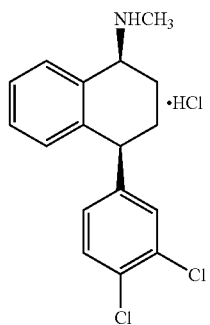

is approved, under the trademark Zoloft®, by the U.S. Food and Drug Administration, as a serotonin re-uptake inhibitor for the treatment of depression, obsessive-compulsive disorder, panic disorder and post-traumatic disorder. Only S-cis sertraline is therapeutically active.

U.S. Pat. No. 4,536,518 describes a synthesis of sertraline hydro chloride from sertralone having the following formula:

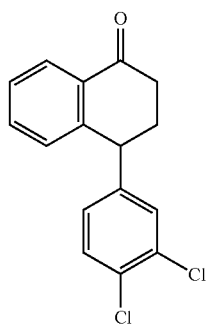

The process for synthesizing sertraline from sertralone has two steps. First, sertralone is condensed with methyl amine in the presence of an acid catalyst, to yield the Schiff base of sertralone, "sertraline-1-imine":

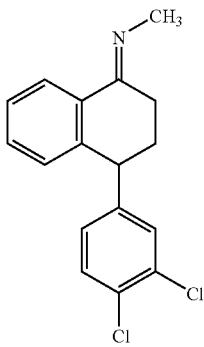

The imine is then reduced to sertraline. The reduction process of U.S. Pat. No. 4,536,518 involves the hydrogenation of sertraline-1-imine concentrate at room temperature for two hours over 10% Pd/C catalyst in an atmosphere of hydrogen (1 atm pressure). The product is a racemic mixture of the cis and trans diastereoisomers ("(±)-cis/trans-sertraline") in the ratio of approximately 3 to 1. The '518 patent discloses that reduction with NaBH$_4$ gives a cis:trans ratio of about 1:1.

As illustrated in the process of the '518 patent, a problem with synthesis of sertraline is the formation of useless stereoisomers which decrease the overall yield. Due to presence of two chiral centers, at C-1 and C-4 (C-4 refers to the carbon next to the dichlorobenzyl group), four different stereoisomers are produced during the synthesis process. Of these, one is sertraline (cis-1S, 4S), and its enantiomer (cis-1R, 4R). The other are trans stereoisomers (1R, 4S) and (1S, 4R).

Sertraline may be isolated in two ways from the other stereoisomers. Isolation of sertraline from the its trans stereoisomers may be done in a classical way by crystallization since distereoisomers have substantially different characteristics. Isolation of sertraline from its enantiomer 1R, 4R-Sertraline may be done by selective precipitation with a chiral entity such as mandelic acid.

U.S. Pat. No. 5,082,970, according to its abstract, discloses a process for converting trans-isomeric sertraline to cis-isomeric sertraline by contacting trans-sertraline, or a mixture of same with up to about an equal part by weight of the corresponding cis-isomer, with a basic equilibration agent like potassium t-butoxide in a reaction-inert polar organic solvent to ultimately afford a cis/trans-mixture wherein the amount of cis-amine present in the mixture achieves a constant value of about 2:1 on a weight-by-weight basis.

WO 01/49638, according to its abstract, discloses a process for converting the cis (1R, 4R), trans (1S, 4R), and trans (1R, 4S) stereoisomers of sertraline into sertraline, starting with an initial reaction mixture which contains at least one of these stereoisomers and converting the sertraline stereoisomers into an imine form of sertraline. The imine form of sertraline is then reduced so that sertraline and at least one sertraline stereoisomer byproduct is produced in the reaction mixture. The sertraline is then recovered from the reaction mixture, e.g., by fractional crystallization (followed by resolution of sertraline from the cis (1R, 4R) stereoisomer, if necessary). The reaction mixture is then recycled through the same steps so that sertraline is produced from its stereoisomers in an asymptotic yield. The reaction scheme of WO 01/49638 requires conversion to an imine before isomerization.

WO 97/21662, according to its abstract, provides a process for racemising an optically-enriched chiral amine of the formula: R1-CH(NR3R4)-R2, wherein R1 is aromatic or unsaturated alkyl; R2 is aromatic or alkyl; and R3 and R4 are independently selected from hydrogen, alkyl and aryl; and wherein any combination(s) of two of the R groups may form a ring; comprises treatment of the optically-enriched amine with a metal hydroxide in an aprotic polar solvent. However, the present Applicants could not isomerize sertraline stereoisomers when carrying out the process of WO 97/21662.

There is a need in the art for recylcing processes which produce sertraline economically on an industrial scale.

SUMMARY OF THE INVENTION

In one aspect, the present invention provides a recycling process for preparing sertraline (1S,4S) comprising:
   a) providing a mixture containing sertralone, mandelic acid, and sertraline distereoisomers (1S,4R), (1S,4S), (1R, 4R) and (1R,4S);
   b) removing sertralone from the mixture;
   c) removing mandelic acid from the mixture;
   d) isomerizing the mixture to increase the 4S to 4R ratio;
   e) oxidizing the isomerized mixture to obtain an imine or a ketone at the 1 position;
   f) reducing the imine to a mixture of 4 stereoisomers or transforming the ketone to the imine and reducing the imine to a mixture of the 4 stereoisomers;
   g) removing sertraline from the mixture; and
   h) optionally repeating steps (a) to (g) or steps (d) to (g).

In another aspect, the present invention provides a halogen free recycling process for preparing sertraline (1S,4S) comprising:
   a) providing a reaction mixture containing sertralone, mandelic acid, and sertraline distereoisomers (1S,4R), (1S,4S), (1R, 4R) and (1R,4S);
   b) removing sertralone from the mixture;
   c) removing mandelic acid from the mixture;
   d) isomerizing the mixture in a two phase system of water, and xylene or toluene, in the presence of tetrabutyl ammonium hydroxide to increase the 4S to 4R ratio, wherein the isomerization increases ratio of trans to cis;
   e) oxidizing the isomerized mixture with potassium permanganate to obtain an imine;
   f) reducing the imine to obtain a reaction mixture with the four stereoisomers;
   g) removing sertraline; and
   h) optionally repeating steps (b) to (g) or (d) to (g).

In another aspect, the present invention provides a recycling process for preparing sertraline (1S,4S) comprising:
   a) providing a reaction mixture containing at least sertraline distereoisomers (1S,4R), (1S,4S), (1R, 4R) and (1R,4S);
   b) isomerizing the mixture to increase the 4S to 4R ratio;
   c) oxidizing the isomerized mixture to obtain an imine or a ketone at the 1 position;
   d) reducing the imine to a mixture of 4 stereoisomers or transforming the ketone to the imine and reducing the imine to a mixture of 4 stereoisomers;
   e) removing sertraline from the mixture; and
   f) optionally repeating steps (a) to (e) or steps (b) to (e).

In another aspect, the present invention provides a recycling process for preparing sertraline (1S,4S) comprising:
   a) providing at least sertraline distereoisomer (1R, 4R);
   b) isomerizing the distereoisome to increase the 4S to 4R ratio;
   c) oxidizing the isomerized mixture to obtain an imine or a ketone at the 1 position;
   d) reducing the imine to a mixture of 4 stereoisomers or transforming the ketone to the imine and reducing the imine to a mixture of the 4 stereoisomers;
   e) removing sertraline from the mixture; and
   f) optionally repeating steps (a) to (e) or steps (b) to (e).

In another aspect, the present invention provides a process for recovering sertralone from a mixture comprising:
   a) providing a mixture containing sertralone and at least one of sertraline distereoisomers (1S,4R), (1S,4S), (1R, 4R) and (1R,4S) in a solvent;
   b) evaporating the solvent to obtain a residue;
   c) preparing an aqueous solution from the residue; and
   d) extracting the solution with a water immiscible solvent;
   e) crystallizing the extracted sertralone.

In another aspect, the present invention provides a process for recovering mandelic acid comprising:
   a) preparing an aqueous solution containing mandelic acid and at least one of sertraline distereoisomers (1S,4R), (1S,4S), (1R, 4R) and (1R,4S) in a solvent; and
   b) extracting the mandelic acid from a water immiscible solvent at a pH of below about 4; and
   c) crystallizing the mandelic acid from the same or different solvent.

DETAILED DESCRIPTION OF THE INVENTION

Figure 1:
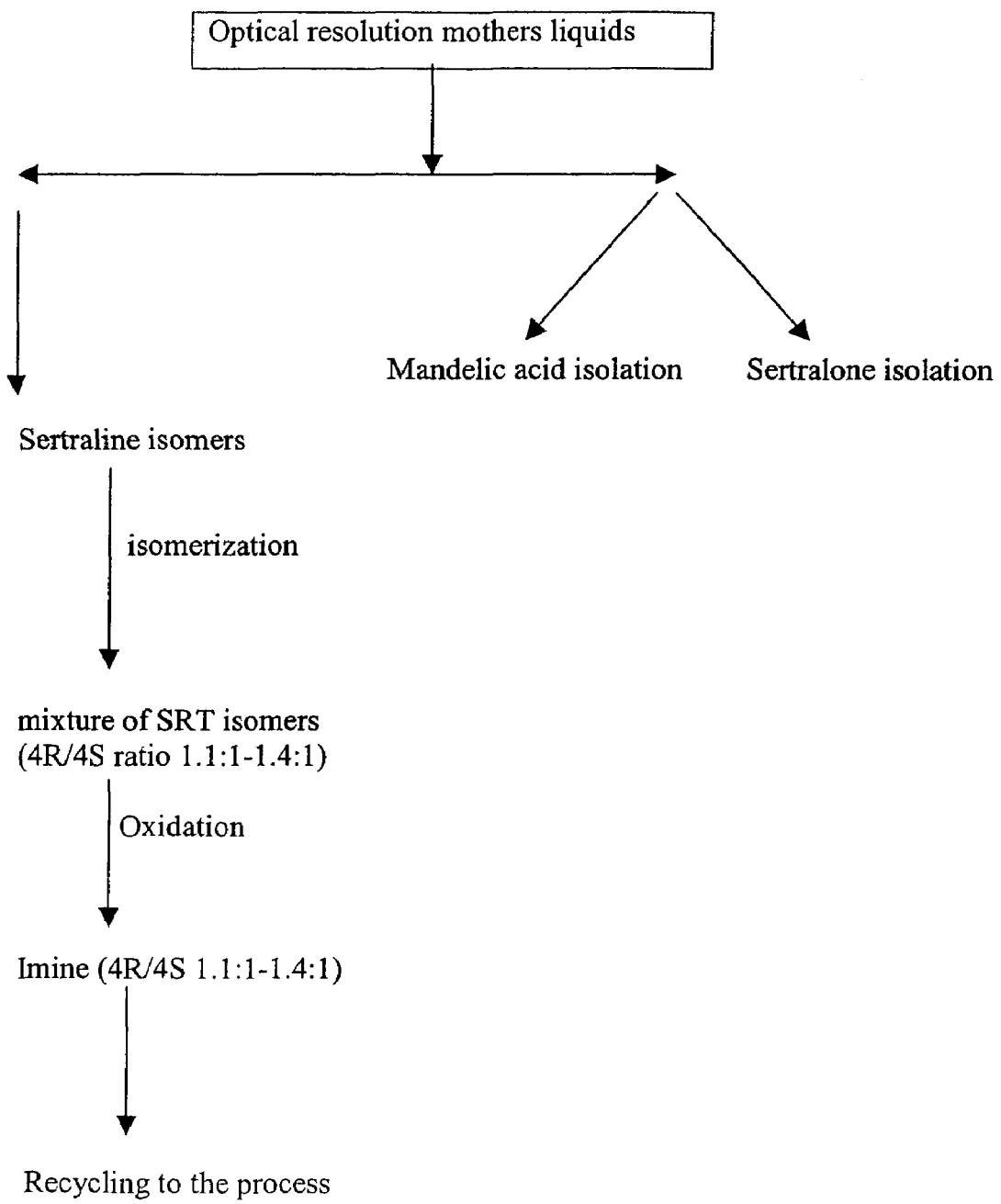
FIG. 1 is a pictorial illustration of the examples of the present invention.

The present invention provides a process for sertraline recovery which obtains a high yield of sertraline compared to the other isomers, and eliminates impurities such as sertralone and mandelic acid.

Along the process for sertraline manufacturing three other isomers are formed and the total yield of sertraline depends in a great measure on the formation ratio of other isomers. Starting from racemic sertralone the sertraline enantiomer 1R,4R-sertraline inherently is formed in the same ratio as sertraline. Most of the sertraline may be recovered by precipitation with optically pure mandelic acid. The recovery of sertraline isomers obtained together with sertraline remaining after such selective precipitation is an important economic aspect of a process for producing sertraline. If optically enriched sertralone is used, it is possible to also end up with pure 1R,4R sertraline.

The present invention provides a process for elimination of sertralone from the mother liquor. To remove sertralone, sertralone is preferably extracted with a water immiscible solvent such as a $C_5$ to $C_{12}$ saturated hydrocarbon, more preferably heptane or hexane, most preferably n-heptane. The hydrocarbon extracts the sertralone from a solvent in which the hydrocarbon is substantially immiscible. Other water immiscible solvents for extraction include $C_2$ to $C_8$ ethers, such as diethyl ether and methyl t-butyl ether (MTBE), $C_1$ to $C_8$ chlorinated aliphatic hydrocarbons such as methylene chloride and chloroform, and $C_4$ to $C_8$ esters such as ethyl acetate and t-butyl acetate. To carry out the extraction, in one embodiment, solvents from the mother liquor, such as ethanol, are removed, such as by evaporation to obtain a residue. The residue is usually an oil remaining after evaporation. The residue is then put in an aqueous solvent, preferably water, and then extracted with the water immiscible solvent such as heptane. Sertraline and its stereoisomers stay in the aqueous phase, while sertralone is extracted with the water immiscible solvent.

After extraction, the sertralone remaining in the mixture is preferably less than about 1%, more preferably of or less than about 0.1%, as an area percentage by HPLC as compared to the combined area of the four isomers.

The extracted sertralone may be washed with an acid to precipitate impurities. Crystallization of sertralone for recycling after the extraction step may be carried from a suitable solvent such as a $C_2$ to $C_8$ ether, including diethyl ether. The temperature of the solvent may be increased to dissolve the sertralone, followed by cooling to a suitable temperature to precipitate sertralone.

The separation and recovery of sertralone allows for recycling of sertralone to further increase the overall yield. The sertralone may then be converted to a methyl amine followed by reduction to obtain the four stereoisomers. The mixture is then subjected to the optical resolution with D(−) mandelic acid and the mother liquor containing sertralone may be extracted again.

The mother liquor may also contain mandelic acid, which is used after the hydrogenation process to precipitate a mandelate salt of (1S,4S) sertraline and remove sertraline from the recycling process. The mandelic acid may be separated by extraction from an aqueous phase at acidic pH at a pH below pKa of mandelic acid (preferably less than about 4, more preferably about 1 to about 2), with a water immiscible solvent such as a $C_3$ to $C_7$ ester, more preferably ethyl acetate, a $C_4$ to $C_7$ ketone such as methyl ethyl ketone or a $C_1$ to $C_8$ chlorinated aliphatic hydrocarbon such as methylene chloride. The mandelic acid may be recovered by crystallization from the ester, and recycled back into the process. Removal of mandelic acid may occur before or after removal of sertralone.

The sertraline isomers are isomerized to increase the ratio of 4S to 4R. Imines are more reactive and unstable compared to amines, and therefore the present invention first isomerizes amines and then oxidizes to obtain an imine.

Being a benzylic carbon, this transformation may occur in basic or acidic conditions. In a preferred embodiment, the isomerization of the amines is carried out in a two phase system of water and a $C_6$ to $C_{12}$ aromatic hydrocarbon, such as toluene or xylene, in the presence of an organic base. An example of an organic base is tetrabutylammonium hydroxide. The reaction is preferably carried out at elevated temperature, more preferably above about 50° C., and most preferably at about reflux temperature. After the reaction, the reaction mixture is preferably cooled to below room temperature, with water being added to form two phases. The organic phase is then separated and washed with water to remove water soluble impurities. The organic phase may then be concentrated by techniques known in the art such as by evaporation or use of a drying agent. The two phase system has milder reaction and produces substantially no side-products.

A one phase system with tetrahydrofuran, DMSO, methyl t-butyl ether, dioxane, mixtures thereof, and a suitable base may also be used. Some solvents give a better ratio after isomerization. Dioxane provided the best result, in relation to DMSO or THF.

The isomerization process preferably results in a decrease of at least about 30% in the ratio of 4R to 4S, more preferably a decrease of about 50%. The ratio at the end of the isomerization process is preferably from about 1.00 to about 1.50 of 4R to 4S. The starting mixture with particular ratios for each isomer is exemplified, but the process of the present invention is applicable to a wide range of varying starting ratios.

The isomerized amines may then be oxidized to obtain an imine or a ketone at $C_1$, thus eliminating the chiral center at $C_1$. Oxidation may be carried out with a hypohalite by using an oxidizing agent such as $Br_2$ in the presence of a base such as sodium hydroxide in a suitable protic solvent such as a $C_1$ to a $C_4$ alcohol. A preferred solvent is methanol.

In a preferred embodiment, the oxidation is carried out with potassium permanganate, which is more environmentally friendly ("green", free of Bromine and other halogenated products as a pollutant) than oxidation with bromine and has a higher yield. Preferably, the oxidation is carried out at a temperature below about room temperature, under basic conditions in an aqueous medium. The aqueous medium may be water optionally in a mixture with a lower alcohol such as methanol or a lower ketone such as acetone. After the reaction, the aqueous layer may be washed with a on organic solvent such as ether to remove impurities. The imine may then be recovered by conventional techniques, such as removal of the solvent by evaporation.

To obtain an amine from the imine, the imine may be hydrogenated according to methods disclosed in WO 98/27050, WO 01/16089, WO 99/57093 or pending U.S. application Ser. No. 60/462,816, incorporated herein by reference. In one embodiment, a cobalt containing catalyst is used for reduction, in a batch reactor or a trickle bed reactor.

After hydrogenation, the four stereoisomers are produced. Sertraline may be separated by fractional crystallization with a chiral precipitating agent such as mandelic acid, while the other stereoisomers may be recycled as disclosed above.

Such fractional crystallization may be carried out with or without separation of cis isomers from trans isomers beforehand.

In addition to conversion of the amines to the imine, it is possible to convert the amines to sertralone, followed by transformation of sertralone to sertraline-imine and hydrogenation.

The sertraline produced in the present invention may then be converted to a polymorphic form of sertraline hydrochloride. Such polymorphic forms, such as Forms II and V, and processes for their preparation, are disclosed in U.S. Pat. Nos. 6,495,721, 6,452,054, 6,500,987 and 6,600,073, incorporated herein by reference. In one embodiment, gaseous HCl is added to a solution of sertraline base or sertraline mandelate in n-butanol at temperature above about 40° C. Preferred pharmaceutical oral dosage forms of sertraline hydrochloride have a dosage of from about 20 mg to about 100 mg base equivalents, and may be administered to a mammal such as a human.

Impurity Profile of Sertraline Hydrochloride by HPLC

| HPLC | |
|---|---|
| Column & packing | Chiradex 250-4, 5μ, Merck 1.51333.0001 |
| Eluent: | 52% ammonium dihydrogen phosphate 0.05M adjusted to pH 4.2 with $H_3PO_4$ 48% methanol |
| Flow rate | 1.0 ml/min. |
| Detector | 220 nm. |
| Sample volume | 20 μl. |
| Diluent | Eluent |
| Oven temperature | 30° C. |

Purity Profile of Sertralone by GC

| GC | |
|---|---|
| Column & packing | BP 5, 30 m × 0.53 mm × 1.0µ, SGE PN 054195 or equivalent column |
| Injector temperature: | 250° C. |
| Detector temperature | 300° C. |
| Oven temperature | 220° C. for 10 minutes than 10° C./minutes up to 250° C. for 3 minutes. |
| Injection volume | 1 µl. |
| Flow | 14 ml/min helium |
| Detector | FID |
| Diluent: | aaHexane |
| Purity profile of imine by GC | |
| Column & packing | BP 5, 30 m × 0.53 mm × 1.0µ, SGE PN 054195 or equivalent column |
| Injector temperature: | 160–180(C. |
| Detector temperature | 300(C. |
| Oven temperature | 220° C. for 10 minutes than 10° C./minutes up to 250° C. for 7 minutes. |
| Injection volume | 1 µl. |
| Flow | 14 ml/min helium |
| Detector | FID |
| Diluent: | Diethyl ether |

EXAMPLES

Example 1

The recovery operation process of sertraline isomers starts from the mother liquor of the optical resolution step. The content of the mother liquors is as follows: ~25% Sertralone, 45% 1R,4R-Sertraline, ~10% Sertraline, ~7% 1R,4S-trans-Sertraline and ~7% 1S,4R-trans-Sertraline, and ethanol. The process may be described in the following scheme illustrated in FIG. 1.

The mother liquor (2 L) from the step sertraline mandelate crude were evaporated to a volume of about 500 mL, cooled with ice-water and 3 N HCl (160 mL) was added carefully to a mixture to maintain the temperature less than 30° C. A precipitate formed and the suspension was stirred for about 30 minutes at the same temperature. The mixture was evaporated under reduced pressure at 25–28° C. to give a yellow solid residue with the following composition provided in Table 1.

TABLE I

Composition of evaporated mixture under reduced pressure at 25–28° C.

| Rt | Area (%) | Comments |
|---|---|---|
| 4.75 | 0.88 | |
| 5.73 | 0.24 | |
| 6.77 | 0.10 | |
| 7.41 | 0.21 | |
| 8.08 | 12.10 | Mandeleic acid |
| 10.56 | 45.35 | (1R, 4R)-SRT |
| 11.49 | 9.85 | (1S, 4S)-SRT |
| 15.09 | 25.19 | Unresolved peak of (1R, 4S)-SRT and Sertralone |
| 18.51 | 6.10 | (1S, 4R)-SRT |

1) Isolation of Sertralone 1.1 Separation of Sertralone From the Mixture

Water (200 mL) was added to the above residue and sertralone was extracted with heptane (200 mL×7) at 60° C. The heptane extracts were combined, dried over sodium, filtered and a sample was taken for GC analysis. According to GC analysis the sample contains about 1.6% of impurity with $R_t$ 7.4. The heptane solution was concentrated to a weight of about 600–700 g and the solution was washed with 1 N solution of hydrochloric acid (50 mL). The sample contained the same impurity on a level about 1.5%. Additional washing with 1 N solution of hydrochloric acid (50 mL) gave the sample with the same impurity (about 1.4%). During washing process a brown resin precipitated directly in a separating funnel.

The solution of sertralone after separation of a resin was washed with water (50 mL×3) to give a material with the same impurity about 1.5%.

The solution was dried over sodium sulfate, filtered and evaporated to a mass about 380 g and a brown oil began to precipitate which contained about 0.32% of the impurity with $R_t$ 7.49 min.

The flask was kept at +4° C. for 2–3 days to precipitate a fine yellow crystals with only 0.10% of the impurity with $R_t$ 7.47 min. A solution was decanted from precipitated sertralone and evaporated to give (5.26 g) with 8.30% of the impurity with $R_t$ 7.48. The precipitate after decantation was dried under reduced pressure to give 22.2 g of dried material (yield 80.7%).

1.2 Crystallization of Sertralone From MTBE (Methyl-t-butyl-ether)

Sertralone (a mixture of an oil and crystals, about 20.5 g) was dissolved under reflux in a minimal amount of MTBE (75 mL), the solution was cooled to 20–25° C., stirred for about 1 h at this temperature and then was kept at 0 plus/minus 5° C. for about 2 h. Precipitated fine yellow crystals were filtered off, dried under reduced pressure at 40–50° C. to a constant weight to give about 10.0 g of material having 99.5% purity (GC) (yield 49%). The mother liquor was concentrated to ½ of a volume and kept overnight in freezer (−11° C.) to give 5.34 g of crystalline material, 97.1% purity by GC (yield 75%).

2. Isolation of the Amines Mixture

After extraction of the solid residue with heptane, a residue free from sertralone was obtained. It was mixed with 2N solution of sodium hydroxide (400 mL) and extracted at 55–60° C. with heptane (200 mL×3). Heptane solution was dried over sodium sulfate and evaporated to give 95.0 g material having the following composition:

TABLE II

Composition of evaporated mixture under pressure at 25–28° C.

| Rt | Area (%) | Comments | 4R to 4S ratio |
|---|---|---|---|
| 4.85 | 0.36 | | 2.77 |
| 5.07 | 0.19 | | |
| 6.80 | 0.24 | | |
| 10.51 | 64.35 | (R, R)-SRT | |
| 11.47 | 13.97 | (S, S) SRT | |
| 14.53 | 12.28 | (1R, 4S)-SRT | |
| 16.29 | 0.11 | Sertralone | |
| 18.53 | 8.45 | (1S, 4R)-SRT | |

3 Separation of D-Mandelic Acid

After extraction of amines from a basic aqueous phase, the extract was mixed with sodium chloride (10–15 g), acidified with 12 N hydrochloric acid (60 mL) to pH 1–2, extracted with ethyl acetate (100 mL×3), dried over sodium sulfate, the extract was filtered to obtain a solution and evaporated to a weight about 50–60 g to obtain a suspension.

The obtained suspension was kept in freezer (−11° C.) for about 3 h, a precipitate was filtered off, washed with cold (0° C.) EtOAc (10–20 mL), dried under reduced pressure to a constant weight to give 24.6 g, 99.76% purity by HPLC. From the Mother liquor a second crop was obtained by evaporation (7.8 g). (The yield of crystallized D-Mandelic acid was about 24.6 g (76%)).

Isomerization of Amines Mixture Free in Toluene With 1.5 M Water Solution of Tetrabutylammonium Hydroxide (TBAH)

A 1-L double-jacketed reactor was charged with a solution of Amines (38 g, 0.12 mol) in Toluene (190 mL) and a 1.5 M solution of tetrabutylammonium hydroxide (100 mL, 0.15 mol, 1.2 eq). The mixture was heated to reflux under vigorous stirring (450 rotations/min) and refluxed for about 56 h while the temperature in vapors was about 87° C. The reaction was monitored by HPLC (Table III).

TABLE III

Isomerization of the amines mixture in bi-phase system Toluene/Water solution of TBAH

| Time (h) | (1R, 4R) (%) | (1S, 4S) (%) | (1R, 4S) (%) | (1S, 4R) (%) | Ratio 4R/4S |
|---|---|---|---|---|---|
| 0 | 64.35 | 13.97 | 12.28 | 18.53 | 2.77 |
| 3 | 55.95 | 13.41 | 20.30 | 9.20 | 1.93 |
| 12 | 48.13 | 13.39 | 27.47 | 9.32 | 1.41 |
| 24 | 45.48 | 13.69 | 28.24 | 8.79 | 1.29 |
| 48 | 49.38 | 13.42 | 26.66 | 9.48 | 1.47 |
| 56 | 48.23 | 13.43 | 27.70 | 9.63 | 1.41 |
|  | 48.10 | 13.46 | 27.62 | 9.50 | 1.40 |

The mixture was cooled to 20–25° C., water (150 mL) was added to a reaction mixture, an organic layer was separated and washed with water (50 mL).

The Organic layer was dried over sodium sulfate and evaporated to give about 37 g of a brown oil (yield 97%).

Oxidation With Bromine of the Racemized Mixture of Amines

Bromine (21.3 g, 0.13 mol) was added dropwise to a solution of 1 amines (37.0 g, 0.12 mol) and sodium hydroxide (29.4 g, 0.73 mol) in methanol (340 mL), while the temperature was maintained between 35–40° C. After stirring for 30 min at 30–35° C., the solid formed was separated by filtration and washed with methanol (40 mL×2). The product was suspended in water (100 mL), stirred for 15 min at 20–25° C. and filtered. The product was washed with water (50 mL×2) and allowed to suck dry. The product was finally dried at 55–60° C. under reduced pressure to give about 19.5 g (52.7%) of yellow solid imines (87.6% purity by GC).

Mother liquor was decanted from the red resin, concentrated to a volume about 150 mL and bromine (about 10 g) was added dropwise keeping temperature 35–40° C. Reaction was stirred at 35–40° C. for about 2 h (TLC control). Precipitate was filtered off, triturated with water (50 mL), washed with methanol (10 mL×2), dried at 50° C. under reduced pressure to a constant weight to give about 5 g of imines (86.70% purity by GC.). The total yield was about 68% (25 g). The combined imine samples have been triturated with heptane (60 mL) for about 3 h at 20–25° C. to give 22.35 g. The material was triturated again with heptane (100 mL) for 6–7 h to give 21.05 g.

a) Isomerization of Amines Mixture in Xylene With Tetrabutylammonium Hydroxide (TBAH)

A 1-L double-jacketed reactor was charged with a solution of amines (25 g, 0.082 mol) in xylene (125 mL) and a 1.5 M solution of tetrabutylammonium hydroxide (65 mL, 0.098 mol, 1.2 eq). The mixture was heated to reflux under vigorous stirring (450 rotations/min) and refluxed for about 24 h while the temperature in vapors was about 97° C.

TABLE IV

HPLC monitoring Isomerization reaction in biphasic system: Xylene/Water solution of TBAH

| Time (h) | (1R, 4R) (%) | (1S, 4S) (%) | (1R, 4S) (%) | (1S, 4R) (%) | Ratio 4R/4S |
|---|---|---|---|---|---|
| 0 | 64.35 | 13.97 | 12.28 | 18.53 | 2.77 |
| 3 | 59.58 | 13.98 | 15.98 | 8.91 | 2.29 |
| 12 | 53.42 | 13.11 | 22.65 | 9.49 | 1.76 |
| 24 | 48.88 | 13.22 | 26.36 | 9.53 | 1.47 |
|  | 48.70 | 13.78 | 26.63 | 9.56 | 1.44 |

The mixture was cooled to 20–25° C., water (100 mL) was added to a reaction mixture, an organic layer was separated and washed with water (20 mL). The organic layer was dried over sodium sulfate and evaporated to give about 24 g (96%) of a brown oil.

b) Oxidation With Bromine of the Racemized Mixture of Amines to Imines

Bromine (11.47 g, 0.07 mol) was added dropwise to a solution of amines (19 g, 0.062 mol) and sodium hydroxide (16.0 g, 0.40 mol) in methanol (180 mL), while the temperature was maintained between 35–40° C. After stirring for 30 min at 35–40° C., the TLC analysis showed the presence of the unreacted amines in the reaction mixture.

More bromine (11.47 g, 0.07 mol) was added dropwise to a reaction mixture at 35–40° C. and the mixture was stirred for about 30 min at this temperature. The solid formed was separated by filtration and washed with methanol (20 mL), suspended in water (100 mL), stirred for 15 min at 20–25° C., filtered off and washed with methanol (20 mL). The product was finally dried at 55–60° C. under reduced pressure to give about 10.6 g of a yellow solid imines (88.8% purity by GC; yield 56%).

A sample of the above material (5.13 g) was crystallized from methyl-t-butyl-ether (MTBE) (100 mL); a solution was cooled to 20–25° C., stirred for 1 h at this temperature, kept overnight at +4° C., filtered off, washed with MTBE (20 mL) and dried to a constant weight to give about 3.0 g (58%) of a pale yellow solid.

Oxidation of Amines to Imines With Potassium Permanganate

A solution of potassium permanganate (10.1 g, 0.064 mol, 4 eq) in water (150 mL) was added dropwise, under vigorous stirring to a solution of the amines mixture (4.8 g, 0.016 mol) in acetone (70 mL), cooled to +5 to +10° C. The mixture was stirred at this temperature for about 5–6 h. A solution of potassium hydroxide (3.6 g) in water (20 mL) as well as MTBE (100 mL) was added to a brown mixture and the suspension was stirred for about 2 h at 20–25° C. The mixture was filtered, and the organic layer was separated; the aqueous layer was washed with MTBE (50 mL×4), dried over sodium sulfate, evaporated to a weight mass about 16 g and kept in freezer at −11° C. for about 1 h. Pale yellow crystals were filtered off, washed with cold MTBE (10 mL, 5 mL) and dried to give about 2.6 g product (97.86% purity by GC; yield 54%).

Isomerization of Sertraline-Amines With TBAH (1.2 eq) in Solution

In the following table are shown the isomerisation experiments performed in one-phase system.

TABLE V

Isomerization Experiments under One-phase system using different solvents

| Solvent | Time of reflux (h) | 4R to 4S ratio | Comments |
|---------|--------------------|----------------|----------|
|         |                    | 2.77           | Starting mixture |
| Dioxane | 3                  | 1.12           |          |
|         | 9                  | 1.15           |          |
|         | 24                 | 1.08           |          |
| Ethanol | 3                  | 2.18           |          |
|         | 9                  | 1.20           |          |
|         | 24                 | 1.19           |          |
| DMSO    | 7                  | 1.08           | Oxidation products are also formed |
|         | 24                 | 1.07           |          |

Example 2

Resolution (±)-Sertraline hydrochloride (5 g) was dissolved in ethanol (20 mL) and KOH powder (85%) was added to the solution. The slurry was stirred at room temperature for 2.5 hrs. After stirring the solids were removed by filtration and the solution was treated with D-(−)-mandelic acid (2.66 g). Precipitation occurred and the stirring was continued for 24 hours. (+)-Sertraline-mandelate was isolated by filtration and washed with ethanol and then dried to yield 2.70 g of (+)-sertraline-mandelate.

Having thus described the invention with reference to particular preferred embodiments and illustrative Example, those in the art will readily appreciate modifications to the invention as described and illustrated that do not depart from the spirit and scope of the invention as disclosed in the specification. The Example is included to aid in understanding the invention but is not to be construed as limiting the scope of the present invention as defined by the embodiments appended hereto. Descriptions of conventional methods that do not aid in understanding the present invention have not been included. Such methods are well known to those of ordinary skill in the art and are described in numerous publications. All references mentioned herein are incorporated in their entirety.

What is claimed is:

1. A recycling process for preparing sertraline (1S, 4S) comprising:
    a) providing a mixture containing sertralone, mandelic acid, and sertraline distereoisomers (1S, 4R), (1S, 4S), (1R, 4R) and (1R, 4S);
    b) removing sertralone from the mixture;
    c) removing mandelic acid from the mixture;
    d) isomerizing the mixture to increase the 4S to 4R ratio;
    e) oxidizing the isomerized mixture to obtain an imine or a ketone at the $C_1$ position;
    f) reducing the imine to a mixture of 4 stereoisomers, or transforming the ketone to the imine and then reducing the imine to a mixture of the 4 stereoisomers;
    g) recovering sertraline from the mixture; and
    h) optionally repeating steps (a) to (g), or steps (d) to (g).

2. The process of claim 1, wherein the mixture obtained after removal of sertraline in step (g) is subjected to the steps (b) to (g).

3. The process of claim 1, wherein the sertralone is removed by extraction of an aqueous phase with a water immiscible solvent.

4. The process of claim 3, wherein the water immiscible solvent is a $C_5$ to a $C_{12}$ hydrocarbon.

5. The process of claim 4, wherein the hydrocarbon compound is saturated.

6. The process of claim 5, wherein the hydrocarbon compound is n-heptane.

7. The process of claim 3, wherein the water immiscible solvent is selected from the group consisting of $C_2$ to $C_8$ ethers, $C_1$ to $C_8$ chlorinated aliphatic hydrocarbons and $C_4$ to $C_8$ esters.

8. The process of claim 1, wherein the sertralone that remains after the removal step of (b) is less than 1% of the HPLC area.

9. The process of claim 6, wherein the sertralone that remains after the removal step of (b) is less than about 0.1% of the HPLC area.

10. The process of claim 1, wherein the mandelic acid is removed by extraction of an aqueous phase with a water immiscible solvent at a pH below about 4.

11. The process of claim 10, wherein the water immiscible solvent is selected from the group consisting of a $C_3$ to $C_7$ ester, $C_4$ to $C_7$ ketones, $C_1$ to $C_8$ aliphatic hydrocarbons and mixtures thereof.

12. The process of claim 11, wherein the ester is ethyl acetate.

13. The process of claim 1, wherein the isomerization results in a 4S to 4R ratio of about 1.00 to about 1.50.

14. The process of claim 1, wherein the oxidation is carried out with potassium permanganate.

15. The process of claim 1, wherein the oxidation is carried out with hypohalite.

16. The process of claim 1, further comprising the step of recovering the sertralone removed in step (b).

17. The process of claim 16, wherein the sertralone is recovered by crystallization from an ether.

18. The process of claim 1, further comprising the step of recovering the mandelic acid removed in step (c).

19. The process of claim 18, wherein the mandelic acid removed in step (c) is recovered by crystallization out of a $C_3$ to $C_7$ ester.

20. The process of claim 1, wherein the isomerization process proceeds from 4R-cis to trans-4S.

21. The process of claim 1, wherein the isomerization process is carried out in a two-phase system.

22. The process of claim 21, wherein the isomerization process is carried out in water and a $C_6$ to $C_{12}$ aromatic hydrocarbon in the presence of an organic base.

23. The process of claim 22, wherein the hydrocarbon is toluene or xylene.

24. The process of claim 22, wherein the organic base is tetrabutylammonium hydroxide.

25. The process of claim 1, wherein the isomerization process is carried out with a one-phase system.

26. The process of claim 25, wherein the solvent is selected from the group consisting of tetrahydrofuran, DMSO, methyl t-butyl ether, dioxane and mixtures thereof.

27. The process of claim 26, wherein the solvent is dioxane.

28. The process of claim 1, further comprising converting the sertraline recovered in step (g) to sertraline HCl.

29. The process of claim 28, wherein the sertraline HCl is sertraline HCl Form II.

30. A halogen free recycling process for preparing sertraline (1S, 4S) comprising:
    a) providing a reaction mixture containing sertralone, mandelic acid, and sertraline distereoisomers (1S, 4R), (1S, 4S), (1R, 4R) and (1R, 4S);

b) removing sertralone from the mixture;
c) removing mandelic acid from the mixture;
d) isomerizing the mixture in a two phase system of water and xylene, or water and toluene, in the presence of tetrabutyl ammonium hydroxide to increase the 4S to 4R ratio, wherein the isomerization increases ratio of trans to cis;
e) oxidizing the isomerized mixture with potassium permanganate to obtain an imine;
f) reducing the imine to obtain a reaction mixture with the four stereoisomers;
g) recovering sertraline; and
h) optionally repeating steps (b) to (g), or (d) to (g).

31. A recycling process for preparing sertraline (1S, 4S) comprising:
a) providing a reaction mixture containing at least sertraline distereoisomers (1S, 4R), (1S, 4S), (1R, 4R) and (1R, 4S);
b) isomerizing the mixture to increase the 4S to 4R ratio;
c) oxidizing the isomerized mixture to obtain an imine or a ketone at the $C_1$ position;
d) reducing the imine to a mixture of 4 stereoisomers, or transforming the ketone to the imine and then reducing the imine to a mixture of 4 stereoisomers;
e) recovering sertraline from the mixture; and
f) optionally repeating steps (a) to (e) or steps (b) to (e).

32. The process of claim 31, wherein the mixture of step (a) contains mandelic acid.

33. The process of claim 31, wherein the mixture of step (b) contains sertralone.

34. The process of claim 31, wherein the oxidizing step in (c) is carried out with potassium permanganate.

35. A recycling process for preparing sertraline (1S, 4S) comprising:
a) providing at least sertraline distereoisomer (1R, 4R);
b) isomerizing the distereoisome to increase the 4S to 4R ratio;
c) oxidizing the isomerized mixture to obtain an imine or a ketone at the $C_1$ position;
d) reducing the imine to a mixture of 4 stereoisomers, or transforming the ketone to the imine and then reducing the imine to a mixture of the 4 stereoisomers;
e) recovering sertraline from the mixture; and
f) optionally repeating steps (a) to (e), or steps (b) to (e).

36. The process of claim 35, wherein the oxidizing is carried out with potassium permanganate.

37. A process for recovering sertralone from a mixture comprising:
a) providing a mixture containing sertralone and at least one of sertraline distereoisomers (1S, 4R), (1S, 4S), (1R, 4R) and (1R, 4S) in a solvent;
b) evaporating the solvent to obtain a residue;
c) preparing an aqueous solution from the residue; and
d) extracting the solution with a water immiscible solvent;
e) crystallizing the extracted sertralone.

38. The process of claim 37, wherein the water immiscible solvent is a $C_5$ to $C_{12}$ hydrocarbon.

39. The process of claim 38, wherein the hydrocarbon is n-hexane or n-heptane.

40. The process of claim 37, wherein the water immiscible solvent is an ether.

41. The process of claim 40, wherein the ether is diethyl ether or methyl t-butyl ether (MTBE).

42. The process of claim 37, wherein the sertralone is crystallized out of an ether.

43. The process of claim 37, wherein the water immiscible solvent is a $C_1$ to $C_8$ chlorinated aliphatic hydrocarbons or a $C_4$ to $C_8$ esters.

44. A process for recovering mandelic acid comprising:
a) preparing an aqueous solution containing mandelic acid and at least one of sertraline distereoisomers (1S, 4R), (1S, 4S), (1R, 4R) and (1R, 4S) in a solvent; and
b) extracting the mandelic acid from a water immiscible solvent at a pH of below about 4; and
c) crystallizing the mandelic acid from the same or different solvent.

45. The process of claim 44, wherein the solvent in step (b) is a $C_3$ to $C_7$ ester.

46. The process of claim 45, wherein the ester is ethyl acetate.

47. The process of claim 46, wherein crystallization is carried out from ethyl acetate.

48. The process of claim 44, wherein the solvent in step (b) is a $C_4$ to $C_7$ ketone or a $C_1$ to $C_8$ chlorinated aliphatic hydrocarbon.

49. The process of claim 32, further comprising removing mandelic acid from the mixture before isomerizing in step (b).

50. The process of claim 33, further comprising removing sertralone from the mixture before oxidizing in step (c).

* * * * *